United States Patent [19]

Schilling, Jr. et al.

[11] Patent Number: 4,608,242

[45] Date of Patent: Aug. 26, 1986

[54] HYDROSILYL-MODIFIED POLYCARBOSILANE PRECURSORS FOR SILICON CARBIDE

[75] Inventors: Curtis L. Schilling, Jr., Croton-on-Hudson, N.Y.; Thomas C. Williams, Ridgefield, Conn.

[73] Assignee: Union Carbide Corporation, Danbury, Conn.

[21] Appl. No.: 623,556

[22] Filed: Jun. 22, 1984

Related U.S. Application Data

[62] Division of Ser. No. 479,745, Mar. 28, 1983.

[51] Int. Cl.$^4$ ............................................. C01B 31/36
[52] U.S. Cl. ...................................... 423/345; 501/88
[58] Field of Search ................ 556/430, 435; 528/12, 528/20, 14; 423/345; 501/88

[56] References Cited

U.S. PATENT DOCUMENTS

| | | | |
|---|---|---|---|
| 2,483,972 | 10/1949 | Goodwin | 260/448.2 |
| 2,697,029 | 12/1954 | Baker et al. | 23/209.1 |
| 2,850,514 | 9/1958 | Knoth | 260/448.2 |
| 4,052,430 | 10/1977 | Yajima et al. | 260/448.2 D |
| 4,100,233 | 7/1978 | Yajima et al. | 423/345 |
| 4,105,455 | 8/1978 | Koga et al. | 106/44 |

FOREIGN PATENT DOCUMENTS

| | | | |
|---|---|---|---|
| 7965799 | 5/1979 | Japan . | |
| 0143803 | 4/1961 | U.S.S.R. | 556/430 |

OTHER PUBLICATIONS

Nefedov et al., *Proc. Acad. Set.*, USSR, 76–8, 154, 76–8, (1964).
"J. Organometal. Chem.", 6, pp. 665–668, 1966.
"J. Organometal. Chem.", 5, pp. 199–200, 1966.
"J.A.C.S.", 86, No. 7, p. 1454, 4/5/64.
Ser. No. 361,106, Mar. 1982, Schilling et al.

*Primary Examiner*—Paul F. Shaver
*Attorney, Agent, or Firm*—Paul W. Leuzzi

[57] ABSTRACT

A novel branched hydrosilyl-modified polycarbosilane which can be pyrolized to obtain improved yields of silicon carbide. This novel branched hydrosilyl-modified polycarbosilane can be prepared in a one-step reaction from mixtures of silane monomers containing vinyl or halomethyl moieties with silane monomers containing hydrosilyl groups.

3 Claims, No Drawings

HYDROSILYL-MODIFIED POLYCARBOSILANE PRECURSORS FOR SILICON CARBIDE

The U.S. Government has rights in this invention pursuant to Contract No. N00014-75-C-1024 awarded by the Office of Naval Research, Department of the Navy.

This application is a division of prior U.S. application Ser. No. 479,745 filed 3-28-83.

FIELD OF THE INVENTION

This application relates to novel branched polycarbosilane compositions containing hydrosilyl groups, to their production from selected monomer systems, and to their use in the production of silicon carbide.

DESCRIPTION OF THE PRIOR ART

Silicon carbide has long been known and appreciated for its chemical inertness, high temperature stability, semi-conductor properties, and especially its extreme hardness. The hardness of silicon carbide approaches that of diamond and boron nitride.

Silicon carbide was originally prepared by reacting inorganic materials, for example silica and a carbon source such as coke or graphite, at extremely high temperatures. More recently, various methods for preparing silicon carbide from organic materials such as silanes and other organic silicon derivatives have been discovered.

One widely reported approach is described in the following references: U.S. Pat. Nos. 4,052,430, 4,100,233, 4,105,455, 4,110,386, 4,117,057, 4,122,139, 4,134,759, 4,147,538, 4,159,259, Japanese Patent Disclosure No. 1979-65,799, Nakamura et al., *Chemical Abstracts*, 91:215596p, and Yajima et al., *Chemistry Letters*, 5, 435-6 (1976). That approach provides hydrosilyl-modified polycarbosilanes, some of which are soluble and thermoformable by standard methods, which can be pyrolized to silicon carbide. These polycarbosilanes are prepared by a pre-pyrolysis/rearrangement/polymerization of cyclic or linear polydimethylsilanes, which in turn are typically prepared from $(CH_3)_2SiCl_2$ and active metals.

More specifically, such prior art requires an active metal condensation of $Me_2SiCl_2$ to polydimethylsilanes (cyclic or linear), which are isolated and converted by application of heat (and pressure in the case of cyclics) to hydrosilyl-modified polycarbosilanes in a separate step, as illustrated by the equations:

xylene

Polycarbosilane

The crude polycarbosilanes so produced are often subjected to further treatments such as vacuum distillation and fractionation by precipitation from a nonsolvent to isolate hydrosilyl-modified polycarbosilanes of particular use in making silicon carbide fibers.

U.S. Pat. No. 4,276,424 discloses the preparation of polysilanes from organohalosilicon hydrides by reaction with an active metal in a solvent.

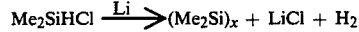

This prior art is cited to exemplify the case in which all the SiH functionality is lost, which differs from the instant invention wherein some of the SiH functionality is retained.

Japanese Kokai Tokyo Koho 78 149,933 (see Chem. Abstr., 90, 138418g (1979)) discloses a preparation of methylhydrogenpolysilanes from reaction of $MeSiHCl_2$ with a methylated disilane mixture. The products are polysilanes, not polycarbosilanes, and clearly differ from the compositions of the instant invention. Similarly, U.S. Pat. Nos. 3,146,248 and 2,146,249 disclose a preparation of SiH-functional polysilanes from reactions of halohydrosilanes with a sodium/potassium alloy in a solvent. The latter compositions are pyrophoric and are intended for use as rocket fuels, rather than as precursors for ceramic compositions. Similarly, U.S. Pat. No. 4,310,482 teaches a chlorine-rich polysilane residue, in which the chlorosilyl groups have been converted to hydrosilyl groups by reduction with lithium aluminum hydride, as a silicon carbide precursor but this is also pyrophoric. This latter polysilane composition also differs chemically from those of the instant invention.

Japanese Kokai Tokyo Koho 79 65,799 (Chem. Abstr., 91, 124210s (1979)) discloses a polysilane prepared from a 44/1/2 molar mixture of $Me_2SiCl_2$/$MeSiHCl_2$/$Me_3SiCl$ using an active metal dispersion in a toluene solvent (Example 7). This polysilane differs chemically from the polycarbosilanes of the instant invention and is too deficient in hydrosilyl groups to be an effective precursor for silicon carbide.

It has also been discovered, as reported in U.S. Ser. No. 361,106 filed Mar. 23, 1982, that branched polycarbosilanes not modified with hydrosilyl groups can be prepared in one step from halosilane mixtures and an active metal in an inert solvent, and that these branched polycarbosilanes can be effectively converted to silicon carbide.

SUMMARY OF THE INVENTION

It has now been found that novel branched hydrosilyl-modified polycarbosilanes which can be pyrolized to obtain improved yields of silicon carbide can also be prepared in a one step reaction from mixtures of simple silane monomers containing vinyl or halomethyl moieties with simple silane monomers containing hydrosilyl groups. More particularly, this invention consists of a process for the production of silicon carbide which comprises, first, reacting at least one compound of the formula

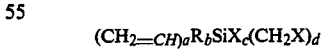

wherein R is lower alkyl, X is halo, a is 0 or 1, b is 0-3, c is 0-4, d is 0-4, a+b+c+d totals 4, and a+d totals at least 1, and at least one compound of the formula $H_dR_e$-$SiX_f$ wherein R is lower alkyl, X is halo, d is 1 or 2, e is 0 -2, f is 1-3, and d+e+f totals 4, such mixture of compounds being selected such that the average molar functionality (as described hereinafter) of the compound system to be reacted is at least 2.3, with an active metal in an inert solvent at an elevated temperature to form a branched polycarbosilane composition containing hydrosilyl groups and, subsequently, pyrolyzing the branched polycarbosilane containing hydrosilyl groups in an inert atmosphere to form ceramic compositions consisting primarily of silicon carbide. The novel branched polycarbosilanes containing hydrosilyl groups themselves constitute a key part of this invention.

DESCRIPTION OF THE PREFERRED EMBODIMENTS

In a broad aspect, this invention contemplates a process for the production of novel branched polycarbosilane compositions containing hydrosilyl groups which comprises reacting, with an active metal in an inert solvent at an elevated temperature, a compound system comprising one or more monomers of formula (I)

(I) $(CH_2=CH)_a R_b SiX_c (CH_2X)_d$ wherein R is lower alkyl (e.g., up to eight carbon atoms since higher carbon contents would only burn off during reaction with a corresponding loss of silicon carbide, and is preferably methyl), X is halo (preferably chloro), a is 0 or 1, b is 0–3, c is 0–4, d is 0–4, a+b+c+d totals 4, and a+c+d totals at least 1, one or more +d totals at least 1, one or more monomers of formula (II)

(II) $H_d R_e SiX_f$ wherein R and X are as defined above, d is 1 or 2, e is 0–2, f is 1–3, d+e+f totals 4, such compound system being selected such that its average molar functionality is at least 2.3 and the formation of silicon-carbon bonds is favored. The monomer compound system of the present invention thus contains at least two different monomers, one of formula (I) and one of formula (II), in monomer ratios such that the average molar functionality of the system is at least 2.3. Such branched polycarbosilanes may be described as compositions which comprise units of the formula:

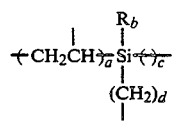

wherein R is lower alkyl (as defined above and preferably methyl), a is 0 or 1, b is 0–3, c is 0–4, d is 0–4, and a+b+c+d totals 4, with the three essential provisos that, in each of the plural units, a, b, c, d, and R may differ (depending on the monomer from which they originate), in at least one unit, a+d must total at least 1 (in order to provide Si—C bonds), and units of the formula:

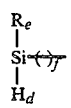

wherein R is as defined above, d is 1–2, e is 0–2, f is 1–3, d+e+f totals 4.

A further aspect of the invention consists in pyrolyzing, the novel branched polycarbosilane compositions containing hydrosilyl groups of the present invention in order to produce silicon carbide and products containing silicon carbide. Pyrolysis is generally performed by heating in a suitable tube under inert atmosphere to the temperature profile of the product, for the purposes of the present invention any means of pyrolyzing known to those skilled in the art may be employed.

The following formulas (wherein R and X have the meanings indicated above) illustrate classes of compounds which can be utilized in the formation of the novel branched polycarbosilanes containing hydrosilyl groups of the present invention:

| Monomers of Formula (I) | |
|---|---|
| $CH_2=CHSiX_2(CH_2X)$ | $CH_2=CHSiX_3$ |
| $CH_2=CHR_2(CH_2X)$ | $R_3Si(CH_2X)$ |
| $CH_2=CHRSiX(CH_2X)$ | $R_2Si(CH_2X)_2$ |
| $SiX_4$ | $RSi(CH_2X)_3$ |
| $R_3SiX$ | $RSiX(CH_2X)_2$ |
| $CH_2=CHR_3Si$ | $RSiX_2(CH_2X)$ |
| $SiX(CH_2X)_3$ | $CH_2=CHRSiX_2$ |
| $SiX_2(CH_2X)_2$ | $CH_2=CHR_2SiX$ |
| $R_2SiX(CH_2X)$ | $RSiX_3$ |
| $R_2SiX_2$ | $SiX_3(CH_2X)$ |

| Monomers of Formula (II) | |
|---|---|
| $X_3SiH$ | $RSiHX_2$ |
| $X_2SiH_2$ | $R_2SiHX$ |

As indicated, it is preferred to use a mixture (i.e. two or more monomer compounds selected from different classes) to make the novel branched polycarbosilanes. Such mixtures include, but are not limited to:

$RSiHX_2/CH_2=CHSiR_3$
$RSiHX_2/CH_2CHSiR_2X$
$RSiHX_2/R_3SiX/CH_2=CHSiRX_2$
$RSiHX_2/R_3SiX/R_2SiX_2/CH_2=CHSiRX_2$
$RSiHX_2/CH_2=CHSiR_2CH_2X$
$RSiHX_2/XR_2SiCH_2X$
$RSiHX_2/R_2Si(CH_2X)_2$

FUNCTIONALITY

One key feature of the present invention is the concept of the average molar functionality, F, of the compound system (i.e. single compound or mixture of compounds) from which the novel branched polycarbosilanes of the invention are made. Specific compounds useful according to the present invention can be assigned specific functionality values, f, as listed below:

| Monomers of Formula (I) | Formula | f |
|---|---|---|
| Trimethylchlorosilane | $Me_3SiCl$ | 1 |
| Dimethyldichlorosilane | $Me_2SiCl_2$ | 2 |
| Methyltrichlorosilane | $MeSiCl_3$ | 3 |
| Tetrachlorosilane | $SiCl_4$ | 4 |
| Chloromethyltrimethylsilane | $Me_3SiCH_2Cl$ | 1 |
| Bis(chloromethyl)dimethylsilane | $Me_2Si(CH_2Cl)_2$ | 2 |
| Tris(chloromethyl)methylsilane | $MeSi(CH_2Cl)_3$ | 3 |
| Tetrakis(chloromethyl)silane + | $Si(CH_2Cl)_4$ | 4 |
| Chloromethyldimethylchlorosilane | $ClCH_2SiMe_2Cl$ | 2 |
| Bis(chloromethyl)methylchlorosilane | $(ClCH_2)_2SiMeCl$ | 3 |
| Tris(chloromethyl)chlorosilane | $(ClCH_2)_3SiCl$ | 4 |
| Chloromethylmethyldichlorosilane | $ClCH 2SiMeCl_2$ | 3 |
| Bis(chloromethyl)dichlorosilane | $(ClCH_2)_2SiCl_2$ | 4 |
| Chloromethyltrichlorosilane | $ClCH_2SiCl_3$ | 4 |
| Vinyltrichlorosilane | $CH_2=CHSiCl_3$ | 5 |
| Vinylmethyldichlorosilane | $CH_2=CHSiMeCl_2$ | 4 |
| Vinyldimethylchlorosilane | $CH_2=CHSiMe_2Cl$ | 3 |
| Vinyltrimethylsilane | $CH_2=CHSiMe_3$ | 2 |
| Vinyldimethylchloromethylsilane | $CH_2=CHSiMe_2CH_2Cl$ | 3 |
| Bis(chloromethyl)-vinylmethylsilane + | $CH_2=CHSiMe(CH_2Cl)_2$ | 4 |
| Vinyltris(chloromethyl)silane + | $CH_2=CHSi(CH_2Cl)_3$ | 5 |

-continued

| Monomers of Formula (I) | Formula | f |
|---|---|---|
| Bis(chloromethyl)vinyl-chlorosilane + | $CH_2=CHSiCl(CH_2Cl)_2$ | 5 |
| Chloromethylvinyldichlorosilane | $CH_2=CHSiCl_2CH_2Cl$ | 5 |
| Chloromethylvinylmethyl-chlorosilane | $CH_2=CHSiMeClCH_2Cl$ | 4 |

| Monomers of Formula (II) | Formula | f* |
|---|---|---|
| Trichlorosilane | $Cl_3SiH$ | 3–4 |
| Methyldichlorosilane | $MeSiHCl_2$ | 2–3 |
| Dimethylchlorosilane | $Me_2SiHCl$ | 1–2 |
| Dichlorosilane | $H_2SiCl_2$ | 2–4 |

*Note that hydrosilyl groups can react with a loss of H and formation of $\equiv SiC\equiv$ or $\equiv SiSi\equiv$ bonds such that functionality varies with the amount of reaction of hydrosilyl groups.

These f values represent the number of bonds which each monomer can form with other molecules, including formation of both $\equiv SiC\equiv$ and $\equiv SiSi\equiv$ bonds, and can be used to calculate average molar functionality values, F, for polycarbosilanes prepared from known mixtures of silane monomers. The chemistry of bond formation is straightforward, involving active metal dehalogenation (1) or desilylation (2) of the vinyl groups.

$$2\equiv SiCl + 2K \rightarrow \equiv SiSi\equiv + 2KCl \equiv SiCl + \equiv CCl + 2K \rightarrow \equiv SiC\equiv + 2KCl \quad (1)$$

$$2\equiv SiCl + CH_2=CHSi\equiv + 2K \rightarrow \equiv SiCH_2 CH(Si\equiv)_2 + 2KCl \quad (2)$$

When monomers of formula (II), i.e., hydrosilyl monomers, are used, a portion of the hydrosilyl groups survive the reactions and yielded hydrosilyl-modified branched polycarbosilanes. Another portion of the hydrosilyl groups undergo reactions wherein the hydrogen (H) is lost and a new bond to silicon or carbon is formed. Hydrosilyl group retention (3) or loss (4) are shown with methyldichlorosilane as a model:

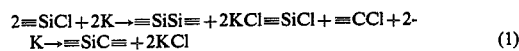

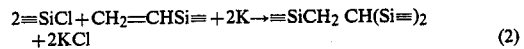

Thus, the f values for monomers of Formula (II) can in fact vary from values representing only $\equiv SiCl$ bonds to values representing combination of $\equiv SiCl$ bonds and a portion of the $\equiv SiH$ bonds.

The molar functionality, F, of a polycarbosilane is identical to that of the compound system from which it is prepared. For a polycarbosilane prepared from a single monomer, F is equal to f. For a polycarbosilane prepared from a mixture, the molar functionality F is dependent upon the molar ratios of the monomers as well as their f values. For example, F for a polycarbosilane prepared from a mixture of monomers having respective functionality values $f_1$, $f_2$, and $f_3$, in the molar ratio x/y/z, can be calculated from the equation:

$$F = \frac{xf_1 = yf_2 = zf_3}{(x+y+z)}$$

Preferred molar functionality values for tractable solid polycarbosilanes are greater than two (F>2) requiring that at least one of the monomers have an f value of 3 or higher, i.e., that the polycarbosilane is branched, rather than linear.

Where f values have ranges as for monomers of Formula (II), the F molar functionality values will also have ranges according to the above equation.

The property which the branched hydrosilyl-modified polycarbosilanes of the present invention possess, namely their ability to be converted into silicon carbide compositions in higher yield than prior art branched polycarbosilanes not modified with hydrosilyl groups is believed to be due to an increase in backbone branching derived from the hydrosilyl groups. While a portion of the hydrosilyl groups increase branching during the preparative reaction by loss of hydrogen functionality, the remainder increase branching in situ during early stages of the pyrolysis process. The degree of branching and the molecular weight can be controlled, by appropriate choices of starting monomer systems and the molar ratios within such monomer systems, such that the products range from soluble oils to the preferred soluble solids to insoluble, infusible solids. Since the branching structures of the polycarbosilanes of the present invention derive from the inherent functionalities of the monomers used, the yield of silicon carbide derived from such polycarbosilanes increases with the relative content of branched units, whether such units derive from the preparative chemistry or are created during the pyrolysis process.

While not wishing to be bound by speculative theory, it appears that branching during pyrolysis occurs by reactions between hydrosilyl groups, generating $\equiv Si-Si\equiv$ bonds, or between hydrosilyl groups and unsaturated groups such as vinyl groups, generating $\equiv SiC\equiv$ bonds.

PROCESSING

In the present invention, a monomer system is reacted with an active metal in an inert solvent at an elevated temperature to generate novel branched hydrosilyl-modified polycarbosilanes.

The preferred active metal is potassium for reasons of high reactivity and low melting point. Other active metals are considered less reactive but they may be used if longer reaction times are acceptable. Alloys, such as potassium/sodium, may also be used. According to the prior art, lithium may destroy all hydrosilyl functionality.

The preferred solvent is anhydrous tetrahydrofuran. However, higher boiling solvents such as dioxane, 1,2-dimethoxyethane, and the like, or hydrocarbons such as toluene, xylene, or octane, and the like, can be used, particularly with the less reactive metals provided the solvent is not reactive with the active metal or the halosilane. Hemamethylphosphoramide may also be used, but it is more costly and is a suspected carcinogen.

The combination of the active metal (potassium) and the solvent (tetrahydrofuran) allows reactions to occur at the reflux temperature of the solvent, which is just above the melting point of the active metal, in this instance potassium. This combination does not allow significant reaction of chlorosilyl groups with the tetrahydrofuran solvent; such reactions have been observed with sodium and magnesium. The combination also allows retention of a portion of the charged hydrosilyl groups.

The polycarbosilane-forming reactions of the present invention can be run in standard laboratory glassware or commercial equipment, under inert atmospheres at atmospheric pressures, with provisions for external heating ano cooling, stirring, and for incremental addition of mixtures of monomers. Thus, the process of the present invention regarding polycarbosilane preparation is not narrowly critical with regard to equipment and requires no extraordinary equipment.

In a typical preparation, a weighted amount of active metal is placed in the inert solvent under an inert atmosphere. Heat is applied to reflux, melting the active metal, and addition of the monomer system is begun, with stirring. The reactions are sufficiently exothermic at controlled addition rates to maintain reflux without application of external heat. After completion of addition, heat may be reapplied for any specified time period. Illustrative examples are supplied below.

Reaction conditions are thus not narrowly critical except that reaction temperature should be maintained above the melting point of the active metal and stirring should be maintained to prevent caking of by-product salts. A slight excess of the active metal is desired to insure consumption of a majority of chlorosilyl groups. Reactions can be terminated by addition of an alkylating agent, such as methyl chloride, or a protic material, such as water. Salt by-products are removed by filtration or water washing, and the mother liquor concentrated by stripping. The resultant polycarbosilane solution can be directly stripped or added to a non-solvent medium such as methanol/acetone, precipitating the tractable solid polycarbosilane fraction, which is collected and dried. The non-solvent mixture can then be stripped to recover a liquid polycarbosilane residue, while the filtered salt can be water-washed to isolate insoluble polycarbosilanes, if any. These reaction procedures are familiar to those skilled in the art and are typical of numerous active metal reactions.

SILICON CARBIDE

The novel branched hydrosilyl-modified polycarbosilanes of the present invention, ranging from soluble oils to insoluble solids, can be converted to silicon carbide compositions by themselves or in mixture with other components as disclosed for prior art polycarbosilanes, simply by heating in an inert atmosphere over specified time periods up to 1200° C. or beyond.

Most useful of the branched hydrosilyl-modified polycarbosilanes of the present invention are those which are, at room temperature, normally solid and soluble in non-protic organo solvents. They can be therm-formed into a variety of shapes such as pellets, fibers, films, etc., or can be dissolved in a variety of solvents including carbon tetrachloride, methylene dichloride, trichloromethane, toluene, tetrahydrofuran, dioxane, and the like, to be cast from solution as films or spun from solution as fibers.

The range of polycarbosilanes can be used as binders for the shaping of infusible, insoluble powders such as silicon carbide or silicon nitride in the same fashion as prior art polycarbosilanes. Both shaped polycarbosilane articles and shaped polycarbosilane-bound articles can be converted to silicon carbide compositions by atmospheric pressure pyrolysis.

The shaping, spinning or casting of the polycarbosilanes of the present invention can be performed in commercially available equipment designed for such purposes and known to those skilled in the art. Similarly, the pyrolyses are also performed in commercially available equipment designed for such work and also known to those skilled in the art. Sintering aids typical of such high temperature reactions may be employed if desired.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

All reactions were run in standard laboratory glassware of various sizes using heating mantles, mechanical stirrers with glass or stainless steel blades, thermometers, wet ice or cooled liquid condensers, and provisions for maintenance of nitrogen or argon atmospheres. Temperatures are reported in Centigrade degrees, and the abbreviarions Me, g, mm, ml, min, hr, and THF represent methyl, gram, millimeter, milliliter, minute, hour, and tetrahydrofuran respectively. Reported yields are based on theoretical yields calculated from the silane mixture charged.

Laboratory pyrolyses were run in quartz reactors in a tube furnace up to 800° C., and in alumina reactors in a second tube furnace from 800° C. to 1200° C. No attempt was made to maximize yields by varying pyrolysis conditions.

EXAMPLE A: F=2.0

Reaction of 1/1 $Me_2SiCl_2/CH_2=CHSiMe_3$ with K in THF.

In a 500 ml three-necked round bottom flask with standard taper fittings were combined 33.6 g (0.86 mol) of K metal chunks and 197.7 g anhydrous THF. The flask was fitted with heating mantle, mechanical stirrer with glass blade, thermometer, addition funnel, and wet ice condenser, plus valves for maintaining an inert argon atmosphere. Flask contents were heated to reflux (66°) melting the K, and addition of a mixture of 52.9 g (0.41 mol) of $Me_2SiCl_2$ and 41.0 g (0.41 mol) of $CH_2=CHSiMe_3$ begun and completed in 45 min. with heat off. An additional 80 ml THF was added near completion of addition to reduce viscosity of the reaction mixture. Heating at reflux was resumed at end of addition and continued for 3 hours, followed by cooling in a wet ice bath and termination by slow addition of a solution of 8.5 g $H_2O$ in 70 ml THF. Removal of salt by-products by filtration, drying of organic reaction mixture over $MgSO_4$, removing the latter by filtration, solvent stripping and vacuum distillation yielded 39.7 g (57.0%) of linear polycarbosilane fluid, b.p. greater than 99°/0.04 mm, having the average structure $[CH_2CH(SiMe_3SiMe_2]_x$.

Pyrolysis of this fluid to only 590° under an inert atmosphre at atmospheric pressure left less than 0.3% ceramic residue. This example confirms that the linear polycarbosilane disclosed by Nefedov et al., *Proc. Acad. Sci:*, USSR, 154, 76-8 (1964), is not an effective precursor for silicon carbide when pyrolized at atmospheric pressure under an inert atmosphere.

EXAMPLE B: F=2.33

Reaction of 2/1 $Me_2SiCl_2/CH_2$=$CHSiMe_2CH_2Cl$ with K in THF

Following the general procedure of Example A, 45.3 g (1.16 mol) of K metal in 406.0 g anhydrous THF was used to dechlorinate a mixture of 56.8 g (0.44 mol) of $Me_2SiCl_2$ and 29.6 g (0.22 mol) of $CH_2$=$CHSiMe_2CH_2Cl$. Workup as in Example A, including neutralization of the reaction mixture with 2.73 g $NH_4Cl$ in 10.7 g $H_2O$ after $H_2O$/THF termination, followed by final neutralization with 5g concentrated HCl, yielded 26.7 g (56.3%) of nonvolatile product, b.p. greater than 100°/0.1 mm. Pyrolysis of the latter to 680° yielded 0.7% of ceramic residue indicating that the product of this example is not an effective precursor for silicon carbide.

EXAMPLE C: F=2.0

Reaction of $ClCH_2SiMe_2Cl$ with K in THF

The procedure of Example A was repeated using 16.7 g (0.42 mol) of K metal, 30.0 g (0.21 mol) of $ClCH_2SiMe_2Cl$, and 194.5 g anhydrous THF. Workup yielded 10.6 (79.2%) of polysilmethylene fluid, b.p. greater thant 70°/0.1 min. Pyrolysis to only 585° C. left less than 1% residue confirming that linear polycarbosilanes such as polysilmethylenes known from Goodwin, U.S. Pat. No. 2,483,972 and Knoth, U.S. Pat. No. 2,850,514, are not effective precursors for silicon carbide when pyrolyzed at atmospheric pressure under an inert atmosphere.

EXAMPLE D: F=2.53

Reaction of 0.85/0.3/1.0 $Me_3SiCl/Me_2SiCl_2/CH_2$=$CHSiMeCl_2$ with K in THF

The procedure of Example A was followed using 436.2 g (11.2 mols) of K metal, 2098.3 g of anhydrous THF, and a mixture of 284.1 g (2.62 mols) of $Me_3SiCl$, 119.2 g (0.92 mol) of $Me_2SiCl_2$, and 434.3 g (3.08 mol) of $CH_2$=$CHSiMeCl_2$. A 5 l flask with a bottom take-off valve was employed. After termination with $H_2O$/THF and neutralization with conc. HCl, salts were removed as an aqueous lower layer by water washing with 2 l $H_2O$. The organic layer was dried and vacuum stripped, yielding 414.7 g (90.0%) of unfractionated soluble solid polycarbosilanes. Pyrolysis of a small sample to 1200° yielded 32.1% of SiC composition. This Example is within the scope of claims of copending application. U.S. Ser. No. 361,106.

EXAMPLE E: F=2.5

Reaction of 1/1 $Me_2SiCl_2/CH_2$=$CHSiMe_2Cl$ with K in THF

The procedure of Example A was followed using 48.6 g (1.24 mol) of K metal, 403.2 g THF, 47.4 g (0.39 mol) of $CH_2$=$CHSiMe_2Cl$, and 50.7 g (0.39 mol) of $Me_2SiCl_2$. Workup yielded 86.6% (48.66 g) of nonvolatile polymer. Pyrolysis of this product to only 700° yielded only 3.0% of SiC composition. This example, which is outside the scope of this invention, shows that polymers which are branched, but not branched at backbone silicon atoms, are not effective SiC precursors.

EXAMPLE 1: F=2.0-2.5

Reaction of 1/1 $MeSiHCl_2/CH_2$=$CHSiMe_3$ with K in THF

The procedure of Example A was followed using 31.64 g (0.81 mol) of K metal, 422.9 g of anhydrous THF, and a mixture of 44.3 g (0.385 mol) of $MeSiHCl_2$ and 38.5 g (0.385 mol) of $CH_2$=$CHSiMe_3$. Workup yielded 24.36 g of soluble solid (44%) b.p. greater than 35°/1.0 mm. Pyrolysis of this material to 1200° yielded 28.5% of SiC composition. Analytical data and pyrolysis results confirm that the use of $MeSiHCl_2$ in this reaction led to formation of trifunctional branching sites in the polymer backbone resulting in effective thermal conversion to SiC. A similarly prepared linear copolymer (see Example A) yielded only 0.3% ceramic residue in pyrolysis to only 590°.

EXAMPLE 2: F=2.4-3.0

Reaction of 1.5/1 $MeSiHCl_2/CH_2$=$CHSiMe_2CH_2Cl$ with K in THF

The procedure of Example A was followed except that a stainless steel stirrer blade was used, nitrogen was used as the inert atmosphere, and the condenser was filled with toluene which was cooled by a stainless steel immersion coil (through which ice water was circulated). The reaction of 13.1 g (0.34 mol) of K metal is 155.0 g anhydrous THF with a mixture of 13.7 g (0.12 mol) of $MeSiHCl_2$ and 10.6 g (0.08 mil) of $CH_2$=$CHSiMe_2CH_2Cl$ yielded, after workup 9.1 g (69.7%) of product, b.p. greater than 92°/0.7 mm. Pyrolysis of the latter to 1200° yielded 27.8% of silicon carbide composition, confirming that the use of $MeSiHCl_2$ instead of $Me_2SiCl_2$ provides for improved yields of silicon carbide when results are compared to those of Example B.

EXAMPLE 3: F=2.0-2.5

Reaction 1/1 $MeSiHCl_2/ClCH_2SiMe_2Cl$ with K in THF

The procedure of Example 2 was followed using 50.6 g (1.29 mol) of K metal, 894.1 g of anhydrous THF, 35.4 g (0.31 mol) of $MeSiHCl_2$, and 44.1 g (0.31 mol) of $ClCH_2SiMe_2Cl$. Workup yielded 24.9 g (69.5%) of product, b.p. greater than 84°/1.6 mm. Pyrolysis of the latter to 680° yielded 11.1% of ceramic composition, representing a higher silicon carbide yield than in Example C, wherein only $ClCH_2SiMe_2Cl$ was used as the monomer.

EXAMPLE 4: F=2.53-2.67

Reaction of 0.85/0.3/1.0 $Me_3SiCl/MeSiHCl_2/CH_2$=$CHSiMeCl_2$

The procedure of Example 2 was followed using a 2 l flask, 106.39 g (2.72 mols) of K metal, 807.1 g of THF, 69.7 g (0.638 mol) of $Me_3SiCl$, 25.9 g (0.225 mol) of $MeSiHCl_2$, and 105.9 g (0.751 mol) of $CH_2$=$CHSiMeCl_2$. Workup yielded 81.3 g of nonvolatile polymer, b.p. greater than 65°/0.5 mm. Pyrolysis of this polymer to 1200° yielded 51.7% of SiC composition. This examples shows the effectiveness of $MeSiHCl_2$ in increasing SiC yield when compared to the use of $Me_2SiCl_2$ in Example D.

EXAMPLE 5: F=2.5-3.0

Reaction of 1/1 $MeSiHCl_2/CH_2$=$CHSiMe_2Cl$ with K in THF

The procedure of Example 2 was followed using 68.53 g (1.75 mol) of K metal, 524.0 g of THF, 63.94 g (0.556 mol) of MeSiHCl$_2$, and 66.72 g (0.556 mol) of CH$_2$=CHSiMe$_2$Cl. Workup yielded 60.8 g (84.8%) of nonvolatile polymer, b.p. greater than 85°/0.1 mm. Pyrolysis of this product to 1200° yielded 31.0% of SiC composition. This example demonstrates the crosslinking effectiveness of MeSiHCl$_2$ when compared to the Me$_2$SiCl$_2$ used in Example E.

EXAMPLE 6: F=2.43-2.57

Reaction of 3/1/3 Me$_3$SiCl/MeSiHCl$_2$/CH$_2$=CHSiMeCl$_2$ with K in THF

The reaction of Example 4 was repeated except that a 3/1/3 ratio of the respective monomers was used. Pyrolysis of the stable solid product to 680° yielded 53.0% of ceramic composition.

EXAMPLE 7: F=2.47-2.59

Reaction of 0.85/0.3/0.3/1.0 Me$_3$SiCl/Me$_2$SiCl$_2$/MeSiHCl$_2$CH$_2$=CHSiMeCl$_2$ with K in THF The procedure of Example 4 was followed, using a ratio of 0.85/0.3/0.3/1.0 of the respective monomers Me$_3$SiCl, Me$_2$SiCl$_2$, MeSiHCl$_2$, and CH$_2$=CHSiMeCl$_2$. Workup and pyrolysis of the resultant soluble solid polymer to 1200° yielded 41.6% of silicon carbide ceramic composition.

EXAMPLE 8: F=2.51-2.6

Reaction of 0.85/0.2/0.2/1.0 Me$_3$SiCl/Me$_2$SiCl$_2$/MeSiHCl$_2$/CH$_2$=CHSiMeCl$_2$ with K in Me$_2$SiCl2/MeSiHCl =CHSiMeCl2 with K in THF The procedure of Example 4 was followed with the monomers Me$_3$SiCl, Me$_2$SiCl$_2$, MeSiHCl$_2$, and CH$_2$=CHSiMeCl$_2$ in the respective molar ratio of 0.85/0.2/0.2/1.0. The resultant stable solid polymer yielded 40.6% of silicon carbide composition in pyrolysis to 1200°.

EXAMPLE 9: F=2.51-2.56

Reaction of 0.85/0.3/0.1/1.0 Me$_3$SiCl/Me$_2$SiCl$_2$/MeSiHCl$_2$/CH$_2$=CHSiMeCl$_2$ with K in THF The procedure of Example 4 was employed with the monomers Me$_3$SiCl, Me$_2$SiCl$_2$, MeSiHCl$_2$, and CH$_2$=CHSiMeCl$_2$ in the respective molar ratio of 0.85/0.3/0.1/1.0. Workup and pyrolysis of rhe stable solid product yielded 35.5% of ceramic composition (1200°), confirming the role of low levels of MeSiHCl$_2$ in improving pyrolysis yield ralative to Example D.

What is claimed is:

1. A process for producing silicon carbide ceramic compositions which comprises a one-step, direct pyrolysis in an inert atmosphere of a branched hydrosilyl-modified polycarbonsilane comprising units of the formula

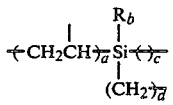

wherein R is a lower alkyl, a is 0 or 1, b is 0-3, c is 0-4, d is 0-4, and a+b+c+d totals 4, with the proviso that, in different units, a, b, c, d, and R may differ, but that, in at least one unit, a+d must total 1 or more and units of the formula

wherein R is defined as above, g is 1-2, e is 0-2, f is 1-3, and g+e+f totals 4.

2. The process of claim 1 for producing silicon carbide ceramic compositions which comprises pyrolyzing in an inert atmosphere a branched, hydrosilyl-modified polycarbonsilane which has been produced by reacting, with an active metal in an inert solvent or mixture of inert solvents at an elevated temperature, a compound system comprising one or more monomers of the formula $$(CH_2=CH)_a R_b SiX_c (CH_2X)_d$$

where R is lower alkyl, X is halo, a is 0 or 1, b is 0-3, c is 0-4, d is 0-4, a+b+c+d total 4, and a +c+d totals at least 1, and one or more monomers of the formula $$H_g R_e SiX_f$$

wherein R and X are defined as above, g is 1 or 2, e is 0-2, f is 1-3, and g+e+f totals 4, said compound system being selected such that its average molar functionality is at least 2.3 and the formation of silicon carbon bonds is favored.

3. The silicon carbide ceramic composition produced by the process of claim 1.

* * * * *